(12) United States Patent
Lin (10) Patent No.: US 9,572,482 B2
(45) Date of Patent: Feb. 21, 2017

(54) ENDOSCOPE WITH A FLEXIBLE CIRCUIT BOARD

(75) Inventor: Rung-De Lin, Taichung (TW)

(73) Assignee: AMBU A/S, Ballerup (DK)

( * ) Notice: Subject to any disclaimer, the term of this patent is extended or adjusted under 35 U.S.C. 154(b) by 6 days.

(21) Appl. No.: 13/566,850

(22) Filed: Aug. 3, 2012

(65) Prior Publication Data

US 2013/0035546 A1    Feb. 7, 2013

(30) Foreign Application Priority Data

Aug. 5, 2011    (TW) .............................. 100214506 U (51) Int. Cl.
| | | |
|---|---|---|
| *A61B 1/04* | (2006.01) | |
| *A61B 1/06* | (2006.01) | |
| *A61B 1/00* | (2006.01) | |
| *A61B 1/05* | (2006.01) | |
| *G02B 23/24* | (2006.01) | |

(52) U.S. Cl.
CPC .......... *A61B 1/0676* (2013.01); *A61B 1/0011* (2013.01); *A61B 1/051* (2013.01); *A61B 1/0684* (2013.01); *G02B 23/2476* (2013.01)

(58) Field of Classification Search
CPC ....... A61B 1/05; A61B 1/051; A61B 1/00105; A61B 1/0011; H04N 5/2253; H04N 5/2251

USPC ......................................................... 600/109
See application file for complete search history.

(56) References Cited

U.S. PATENT DOCUMENTS

| | | | |
|---|---|---|---|
| 8,216,127 B2* | 7/2012 | Zifeng et al. ................. 600/112 |
| 2008/0231723 A1* | 9/2008 | Yonemitsu et al. ....... 348/222.1 |
| 2009/0105538 A1* | 4/2009 | Van Dam ........... A61B 1/00103 600/109 |
| 2009/0322867 A1* | 12/2009 | Carrey ............... A61B 1/00039 348/77 |
| 2010/0185052 A1* | 7/2010 | Chang ........................... 600/112 |
| 2011/0118549 A1* | 5/2011 | Han .............................. 600/109 |
| 2011/0263942 A1* | 10/2011 | Chen ............................. 600/178 |
| 2013/0271588 A1* | 10/2013 | Kirma et al. ................... 348/76 |
| 2013/0274551 A1* | 10/2013 | Kirma et al. ................. 600/104 |

* cited by examiner

*Primary Examiner* — Anhtuan T Nguyen
*Assistant Examiner* — Alexandra Newton
(74) *Attorney, Agent, or Firm* — Faegre Baker Daniels LLP (57) ABSTRACT

An endoscope with a flexible circuit board comprises: a base mounting frame, a flexible circuit, a photosensitive element, a plurality of light emitting elements and a camera. The flexible circuit board, the photosensitive element, the light emitting elements and the camera can be mounted on the mounting frame, and then the mounting frame can be assembled in a pipe to form the endoscope, which greatly improves the ease of assembly, and consequently reducing the labor cost required for assembly. Furthermore, the flexibility of the circuit board reduces the volume of the endoscope and improves applicability.

18 Claims, 7 Drawing Sheets

ENDOSCOPE WITH A FLEXIBLE CIRCUIT BOARD

BACKGROUND OF THE INVENTION

Field of the Invention

The present invention relates to an endoscope, and more particularly to an endoscope with a flexible circuit board.

Description of the Prior Art

Figure 1:
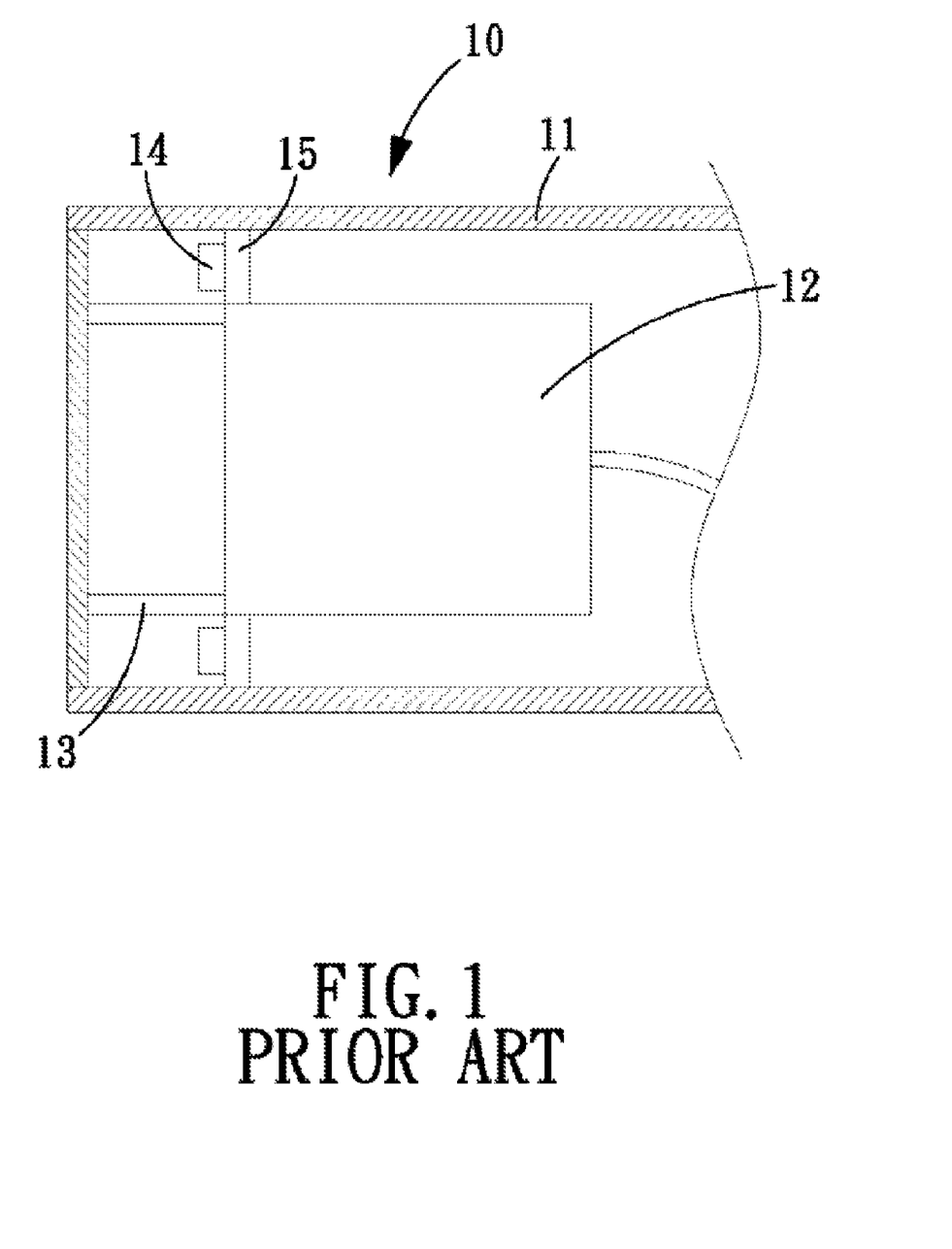
FIG. 1 is a cross sectional view of a conventional endoscope.
Figure 2:
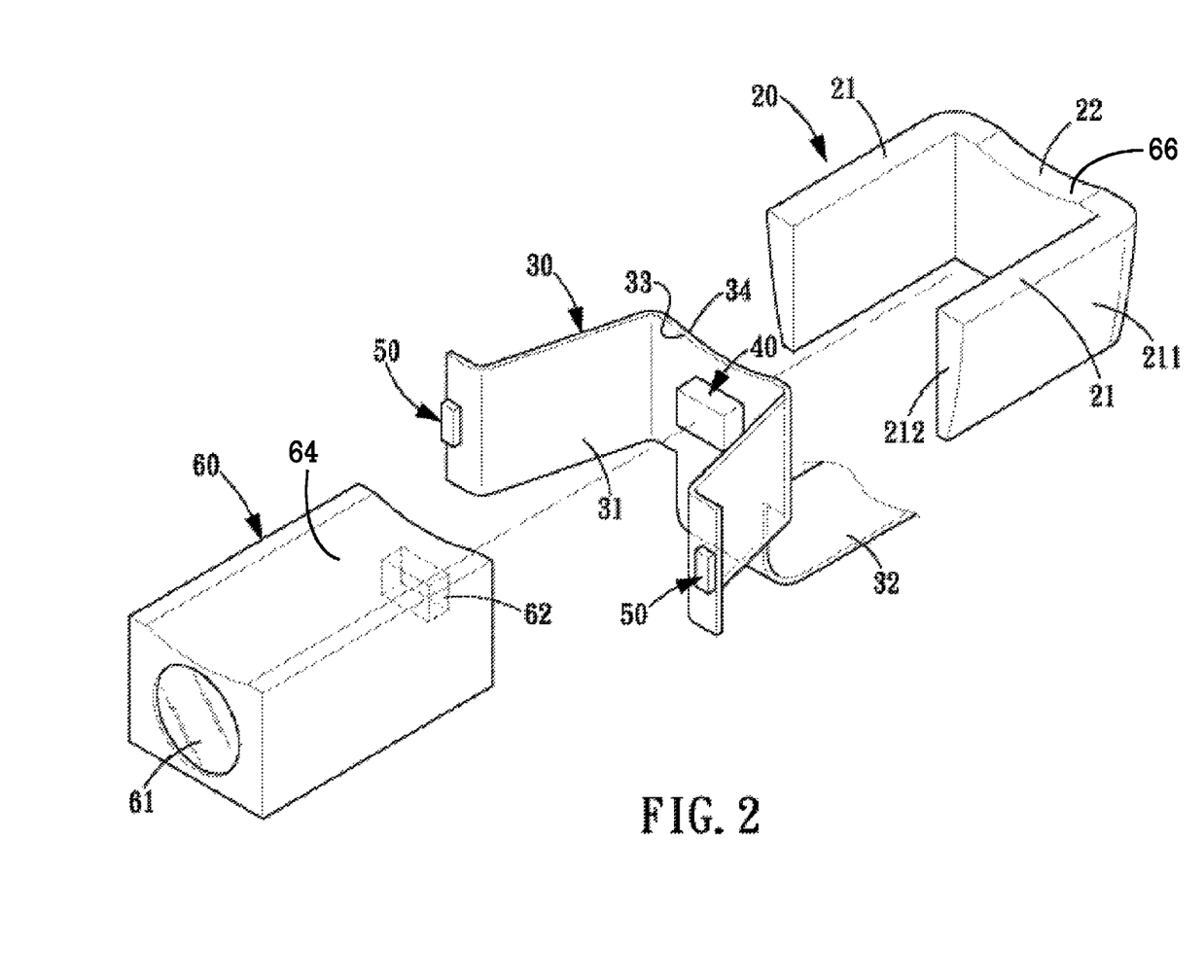
FIG. 2 is an exploded view of an endoscope with a flexible circuit in accordance with a first embodiment of the present invention.
Figure 3:
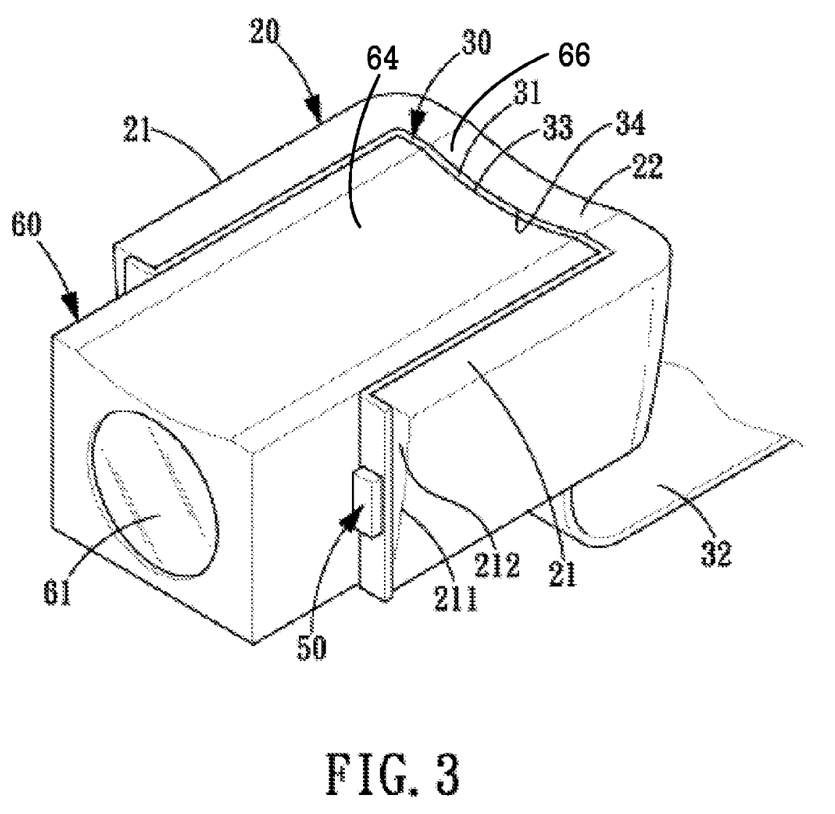
FIG. 3 is a perspective assembly view of the endoscope with a flexible circuit in accordance with the first embodiment of the present invention.
Figure 4:
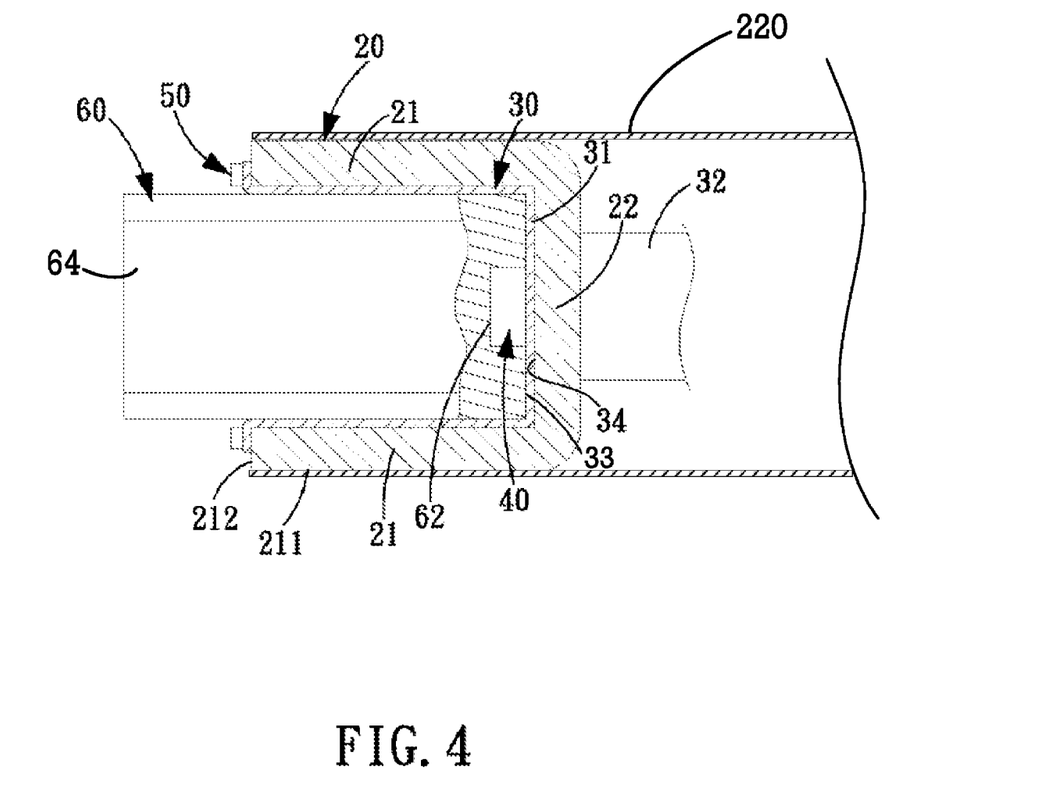
FIG. 4 is a cross sectional view of the endoscope with a flexible circuit in accordance with the first embodiment of the present invention.
Figure 5:
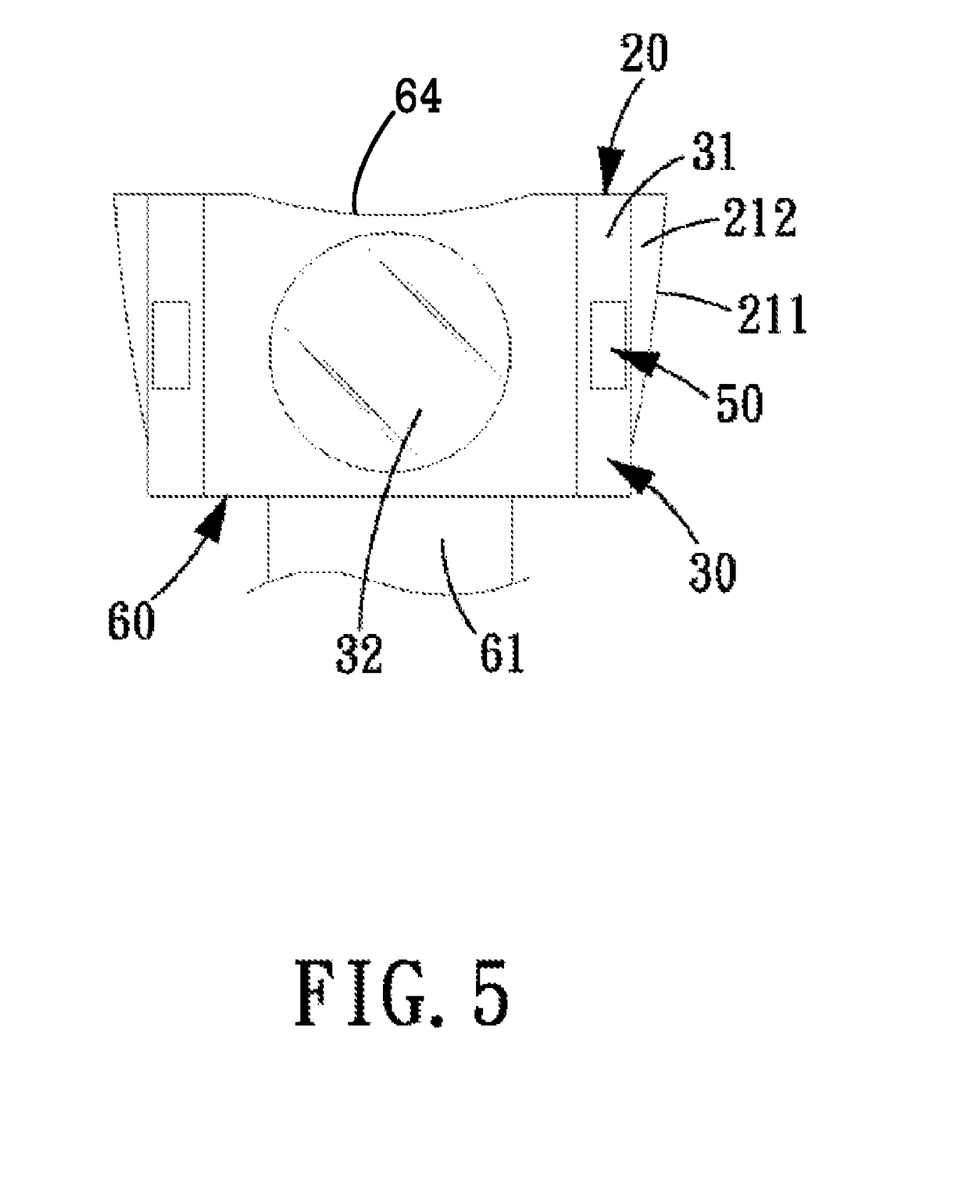
FIG. 5 is a front view of a part of the endoscope with a flexible circuit in accordance with the first embodiment of the present invention.

FIG. 1 shows a conventional endoscope 10 which comprises a pipe 11, a camera 12, a light shield 13 and a plurality of LED (light emitting diode) elements 14 mounted on a circuit board 15 and located around the periphery of the camera 12. The light shield 13 is located at the front of the camera 12 to block light. The camera 12 is combined with the light shield 13 and the LED elements 14 and then disposed in the pipe 11, and the pipe 11 is used to insert in a patient's body cavity.

The endoscope 10 is very small and compact in order to insert into the body cavity, hence, it is very difficult to assemble these parts, including the camera 12, the light shield 13, the LED elements 14 and the circuit board 15 together into such a small pipe 11.

On the other hand, the LED elements 14 and the circuit board 15 have to be arranged around the camera 12, and the conventional circuit board 15 is usually made of rigid metal. Hence, arranging the circuit board 15 around the camera 12 would increase the volume of the endoscope 10.

The present invention has arisen to mitigate and/or obviate the afore-described disadvantages.

SUMMARY OF THE INVENTION

The primary object of the present invention is to provide an endoscope with a flexible circuit board, wherein the flexible circuit board cooperates with the base mounting frame to better fit into a pipe of the endoscope, so as to improve the ease of assembly. Further, the flexibility of the circuit board reduces the volume of the endoscope and improves applicability.

To achieve the above object, an endoscope with a flexible circuit board in accordance with the present invention comprises: a base mounting frame, a flexible circuit, a photosensitive element, a plurality of light emitting elements and a camera. The base mounting frame includes two arm portions and a connecting portion connected between the two arm portions, a surface of the base mounting frame located between the two arm portions and the connecting portion is defined as an inner surface, and another surface opposite the inner surface is defined as an outer surface of the base mounting frame. Each of the two arm portions has an end surface. The flexible circuit board is formed by a mounting portion and an electric connecting portion connected to the mounting portion and includes a mounting surface and a connecting surface. The connecting surface of the flexible circuit board is fixed against the inner surface of the base mounting frame in such a manner that the mounting portion is abutted against the end surfaces, the arm portions and the connecting portion of the base mounting frame, and the electric connecting portion extends out of the base mounting frame to electrically connect to a power supply or an imaging device. The photosensitive element is electrically connected to the mounting portion of the flexible circuit board and mounted on the mounting surface and located in alignment with the connecting portion of the base mounting frame. The light emitting elements are electrically connected to the mounting portion of the flexible circuit board and located in alignment with the end surfaces of the arm portions of the base mounting frame. The camera includes a lens at one end and an engaging groove at another end thereof and is disposed at the mounting portion of the flexible circuit in such a manner that the engaging groove is engaged with the photosensitive element, and the camera protrudes out of the end surfaces of the arm portions of the base mounting frame.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Referring to FIGS. 2-5, an endoscope with a flexible circuit board in accordance with a first embodiment of the present invention comprises: a base mounting frame 20, a flexible circuit board 30, a photosensitive element 40, a plurality of light emitting elements 50 and a camera 60.

The base mounting frame 20 is a U-shaped structure which includes two arm portions 21 and a connecting portion 22 connected between the two arm portions 21. A surface of the base mounting frame 20 located between the two arm portions 21 and the connecting portion 22 is defined as an inner surface, and another surface opposite the inner surface is defined as an outer surface of the base mounting frame 20. Each of the two arm portions 21 has an arc-shaped outer surface 211 and an end surface 212. The connecting portion 22 has a second arcuate recess 66 adjacent an arcuate recess 64 of the camera 60 extending from a proximal end to a distal end of the camera 60.

The flexible circuit board 30 is a T-shaped structure formed by a mounting portion 31 and an electric connecting portion 32 connected to the mounting portion 31 and includes a mounting surface 33 and a connecting surface 34. The connecting surface 34 of the flexible circuit board 30 is fixed against the inner surface of the base mounting frame 20 in such a manner that the mounting portion 31 is abutted against the end surfaces 212, the arm portions 21 and the connecting portion 22 of the base mounting frame 20, and the electric connecting portion 32 extends out of the base mounting frame 20 to be electrically connected to a power supply or an imaging device (not shown).

The photosensitive element 40 is electrically connected to the mounting portion 31 of the flexible circuit board 30 and mounted on the mounting surface 33 and located in alignment with the connecting portion of the base mounting frame 20. The light emitting elements 50 are light emitting diodes electrically connected to the both ends of the mounting portion 31 of the flexible circuit board 30 and located in alignment with the end surfaces 212 of the arm portions 21 of the base mounting frame 20.

The camera 60 includes a lens 61 at one end and an engaging groove 62 at another end thereof and is disposed at the mounting portion 31 of the flexible circuit board 30 in such a manner that the engaging groove 62 is engaged with the photosensitive element 40, and the camera 60 protrudes out of the end surfaces 212 of the arm portions 21 of the base mounting frame 20.

When in assembly, the photosensitive element 40 and the light emitting elements 50 are electrically connected to and mounted on the flexible circuit board 30, then the flexible circuit board 30 is abutted against the inner surface of the base mounting frame 20, and then the camera 60 is mounted on the flexible circuit board 30. By such arrangements, all the parts, including the flexible circuit board 30, the photosensitive element 40, the light emitting elements 50 and the camera 60, can be mounted on the mounting frame 20, and then the mounting frame 20 carrying all the parts can be assembled in a pipe 220 (shown in FIG. 4) to form an endoscope, which greatly improves the ease of assembly, and consequently reducing the labor cost required for assembly.

Furthermore, the flexible circuit board 30 is flexible, so it can be closely abutted against the inner surface of the base mounting frame 20, thus avoiding unnecessary increase in volume of the endoscope. The flexible circuit board 30 is flexible to fit the bending shape of the base mounting frame 20, and the base mounting frame 20 is designed to adapt to different pipes, namely, the flexibility of the flexible circuit board 30 improves applicability. Moreover, the outer surface 211 of the arm portions 21 of the base mounting frame 20 are arc-shaped to better fit into the normally circular-shaped pipe 220 of an endoscope.

On the other hand, the flexible circuit board 30 is abutted against the base mounting frame 20, the light emitting elements 50 are aligned with the end surfaces 212 of the arm portions 21 of the base mounting frame 20, and the camera 60 protrudes out of the end surfaces 212 of the arm portions 21 of the base mounting frame 20, namely, the lens 61 of the camera 60 is located in front of the light emitting elements 50. By such arrangements, the camera 60 itself can block the light of the light emitting elements 50 from reaching the lens 61, so the endoscope of the present invention doesn't require the use of a light shield, which reduces material cost required for production.

Figure 6:
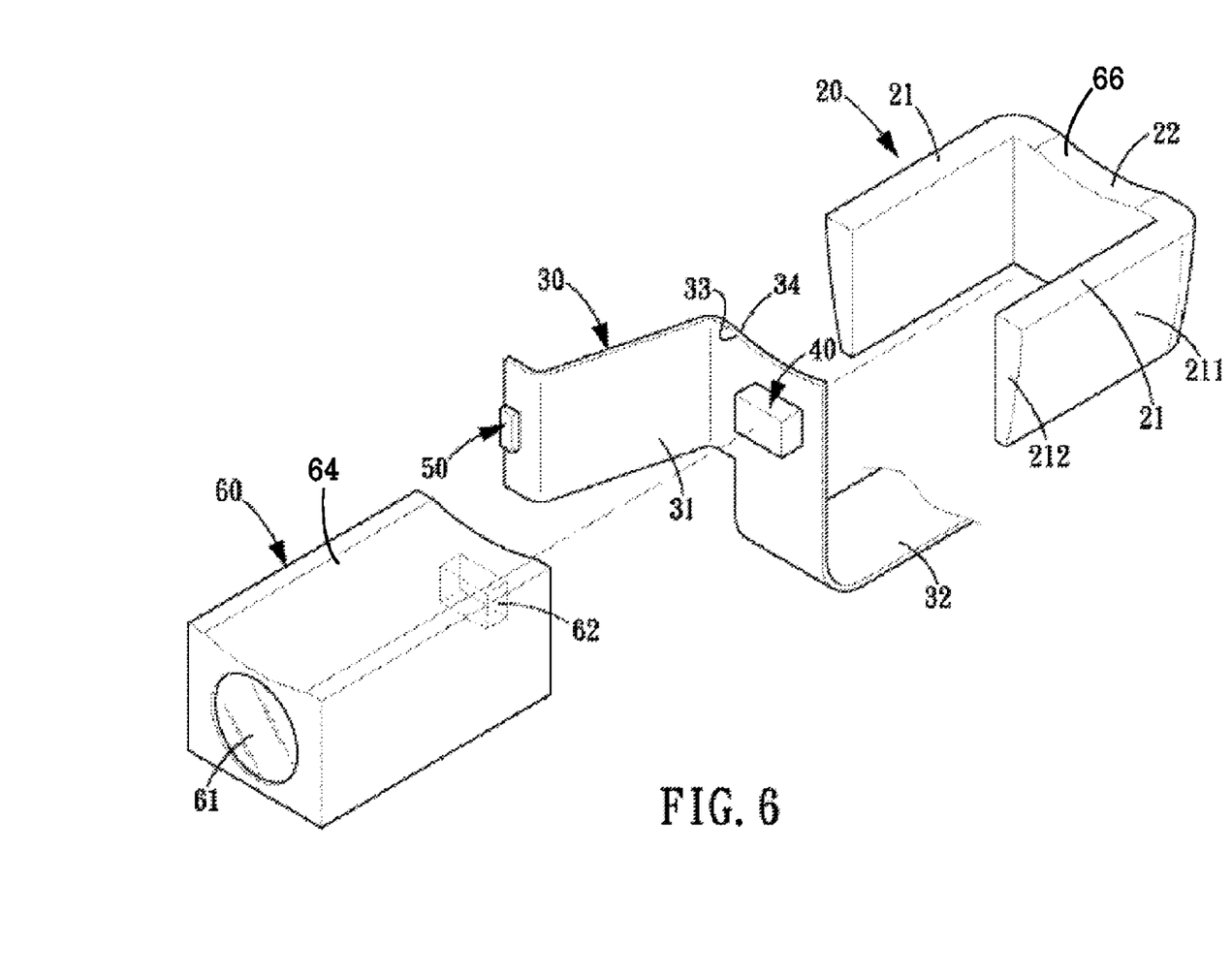
FIG. 6 is an exploded view of an endoscope with a flexible circuit in accordance with a second embodiment of the present invention.
Figure 7:
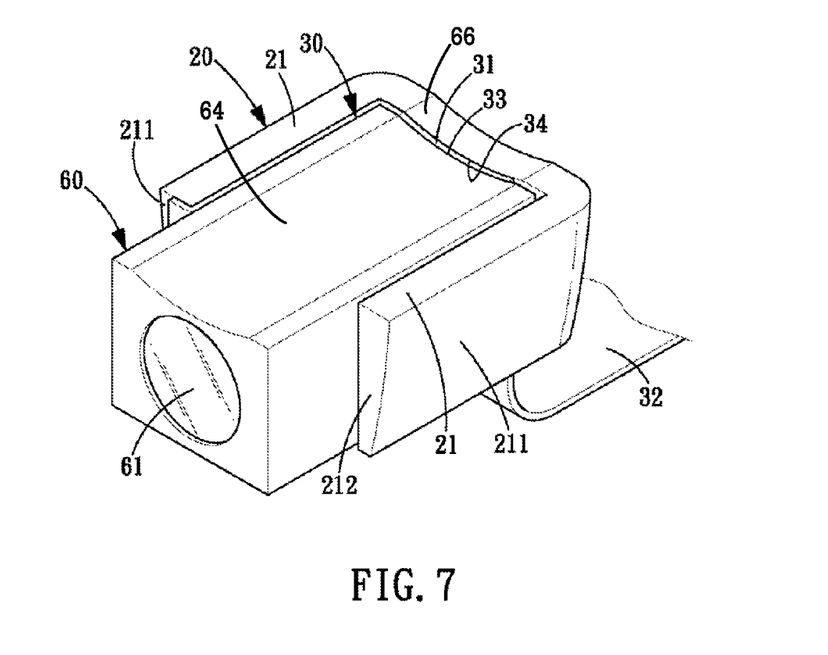
FIG. 7 is a perspective assembly view of the endoscope with a flexible circuit in accordance with the second embodiment of the present invention.

Referring then to FIGS. 6 and 7, a second embodiment of an endoscope of the present invention is similar to the previous embodiment, except that: there is only one light emitting element 50 is disposed on the flexible circuit board 30, and the length of the mounting portion 31 of the flexible circuit board 30 of this second embodiment is reduced as compared to that of the first embodiment.

While we have shown and described various embodiments in accordance with the present invention, it is clear to those skilled in the art that further embodiments may be made without departing from the scope of the present invention.

What is claimed is:

1. An endoscope comprising:
a base mounting frame comprising a unitary structure including two arm portions and a connecting portion fixedly connected to the two arm portions, each of the two arm portions having a length, a width, a thickness, an inner-facing surface along the length and the width, and an end surface;
a flexible circuit board formed by a mounting portion and an electric connecting portion connected to the mounting portion, the mounting portion including a circuit board connecting portion and a circuit board arm portion extending from the circuit board connecting portion and having a length, a width, a thickness, and an outer-facing surface along the length and the width, the outer-facing surface abutting the inner-facing surface of one of the two arm portions, and the electric connecting portion extending out of the base mounting frame to electrically connect to a power supply;
a photosensitive element electrically connected to the mounting portion of the flexible circuit board and parallel to the connecting portion of the base mounting frame;
a light emitting element electrically connected to the circuit board arm portion; and
a camera including a lens, the camera received by the base mounting frame between the two arm portions in such a manner that the circuit board arm portion is between and abuts the camera and one of the two arm portions of the base mounting frame, the circuit board connecting portion is between and abuts the camera and the connecting portion of the base mounting frame, and the photosensitive element is located between the base mounting frame and the lens,
wherein the camera further comprises a first surface and second surface opposite the first surface, the first surface and the second surface being parallel to each other and perpendicular to the connecting portion of the base mounting frame, and a first arcuate recess on the first surface extending from a proximal end to a distal end of the camera, and
wherein the connecting portion of the base mounting frame further comprises a second arcuate recess aligned with the first arcuate recess when the camera is received by the base mounting frame.

2. An endoscope as in claim 1, wherein the light emitting element is located distally from and in longitudinal alignment with the one of the two arm portions of the base mounting frame, wherein a plane parallel to and passing through the one of the two arm portions intersects the light emitting element.

3. An endoscope as in claim 2, wherein the light emitting element is adjacent the end surface of the one of the two arm portions and positioned between the end surface and the lens of the camera, and the camera extends distally from the end surface past the light emitting element to shield the lens from light emitted by the light emitting element.

4. An endoscope as in claim 1, wherein outer surfaces of the two arm portions are arc-shaped.

5. An endoscope as in claim 1, further comprising a second light emitting element longitudinally aligned with the other of the two end surfaces of the two arm portions of the base mounting frame, wherein a plane parallel to and passing through the other of the two arm portions intersects the second light emitting element.

6. An endoscope comprising:
a base mounting frame comprising a U-shaped unitary structure including two arm portions and a connecting portion fixedly connected to the two arm portions, the base mounting frame having an inner surface and an outer surface opposite the inner surface, each of the two arm portions having a length, a width, a thickness, the inner surface extending along the length and the width, and an end surface;
a flexible circuit board comprising a T-shaped structure formed by a mounting portion and an electric connecting portion connected to the mounting portion, the mounting portion including a circuit board connecting portion and a circuit board arm portion extending from the circuit board connecting portion, the circuit board arm portion having a length, a width, a thickness, and an outer-facing surface along the length and the width, the outer-facing surface abutting the inner surface of one of the two arm portions, and the electric connecting portion extending out of the base mounting frame to electrically connect to a power supply;
a photosensitive element electrically connected to the mounting portion of the flexible circuit board;
a light emitting element electrically connected to the circuit board arm portion; and
a camera including a lens, the camera received by the base mounting frame between the two arm portions in such a manner that the circuit board arm portion is between and parallel to the camera and one of the two arm portions of the base mounting frame, the circuit board connecting portion is between and parallel to the camera and the connecting portion of the base mounting frame, and the photosensitive element is located between the base mounting frame and the lens,
wherein the camera and the connecting portion of the base mounting frame are separated in the longitudinal direction by a distance substantially equal to the thickness of the circuit board connecting portion.

7. An endoscope as in claim 6, further comprising a pipe, the camera, the photosensitive element, the light emitting element, the base mounting frame, and the flexible circuit board forming a camera assembly received by the pipe.

8. An endoscope as in claim 7, wherein each of the two arm portions comprises an outer surface arc-shaped to match an internal surface of the pipe and reduce a volume of the endoscope.

9. An endoscope comprising:
a camera including a lens at a distal end thereof, a cavity at a proximal end thereof opposite the lens, and an arcuate recess on an external surface of the camera extending from the proximal end to the distal end of the camera;
a photosensitive element;
a light emitting element;
a base mounting frame comprising a unitary structure including two arm portions and a connecting portion fixedly connected to and between the two arm portions, the base mounting frame configured to receive at least a portion of the camera between the two arm portions, each of the two arm portions having a length, a width, a thickness, an inner-facing surface along the length and the width;
a flexible circuit board having a mounting portion including a circuit board connecting portion connected to a circuit board arm portion, the circuit board arm portion having a length, a width, a thickness, and an outer-facing surface along the length and the width, the circuit board arm portion positioned between and parallel to the camera with the outer-facing surface abutting the inner-facing surface of one of the two arm portions of the base mounting frame, and the circuit board connecting portion positioned between and parallel to the camera and the connecting portion of the base mounting frame;
the light emitting element mounted to the circuit board arm portion and longitudinally positioned intermediate the proximal end and the distal end of the camera; and
the photosensitive element mounted to the circuit board connecting portion and received by the cavity of the camera when the camera is received by the base mounting frame,
wherein the camera and the connecting portion of the base mounting frame are separated in the longitudinal direction by a distance substantially equal to the thickness of the circuit board connecting portion.

10. An endoscope as in claim 9, further comprising:
a second circuit board arm portion connected to the circuit board connecting portion; and
a second light emitting element mounted to the second circuit board arm portion and longitudinally positioned intermediate the proximal end and the distal end of the camera.

11. An endoscope as in claim 9, wherein each of the two arm portions comprises an end surface, and the circuit board arm portion comprises a free end on which the light emitting element is mounted, the free end abutting one of the two end surfaces.

12. An endoscope as in claim 9, further comprising a pipe, the camera, the photosensitive element, the light emitting element, the base mounting frame, and the flexible circuit board forming a camera assembly received by the pipe.

13. An endoscope as in claim 12, wherein each of the two arm portions comprises an outer surface arc-shaped to reduce a volume of the endoscope.

14. An endoscope as in claim 1, the mounting portion of the flexible circuit board further comprising a second circuit board arm portion extending from the circuit board connecting portion.

15. An endoscope as in claim 14, wherein the base mounting frame has a height which is substantially equal to a height of the circuit board arm portion and the second circuit board arm portion.

16. An endoscope as in claim 14, wherein the circuit board connecting portion is substantially coextensive with the circuit board arm portion.

17. An endoscope as in claim 6, wherein the circuit board arm portion is between the camera and the one of the two arm portions of the base mounting frame without a gap therebetween.

18. An endoscope as in claim 17, wherein the circuit board arm portion contacts the camera and the one of the two arm portions of the base mounting frame.

* * * * *